Oct. 8, 1957 F. W. ANDERSON Plant Pat. 1,646
NECTARINE TREE
Filed Feb. 7, 1957
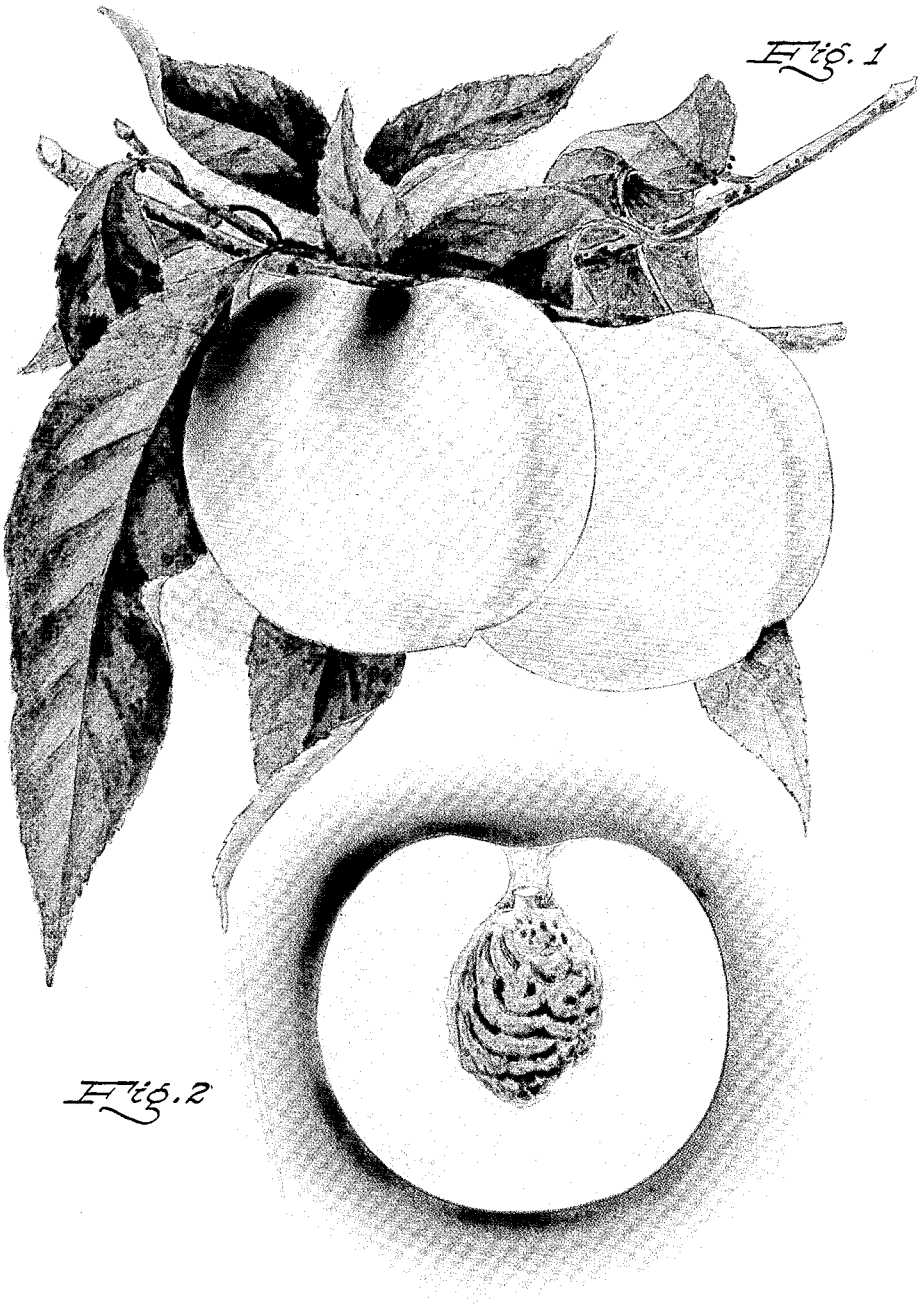
WITNESS
Addison E. Avery
INVENTOR
Frederic W. Anderson
BY Webster & Webster
ATTYS.

United States Patent Office

Plant Pat. 1,646
Patented Oct. 8, 1957

1,646

NECTARINE TREE

Frederic W. Anderson, Merced, Calif.

Application February 7, 1957, Serial No. 638,887

1 Claim. Cl. (47—62)

This invention relates to a new and distinct variety of nectarine tree which has a relatively low winter chilling requirement, and which tree bears large, firm, yellow-fleshed, freestone fruit whose skin is smooth surfaced, and of yellow ground color largely overspread with a bright red, shading from orange.

The present variety of nectarine tree is the result of an F-1 cross between the clingstone Le Grand nectarine (United States Plant Patent No. 549) and the freestone Sun Grand nectarine (United States Plant Patent No. 974).

The variety was originated by me in the course of an extensive and continuing plant breeding program conducted at my experimental orchard located near Le Grand, Merced County, California; an important purpose of such program being to seek and obtain better nectarine varieties having commercial market potential and particular harvest periods.

When the seedling resultant from the above cross first produced fruit, it appeared to have the attributes of a quite desirable commercial variety of nectarine, and I therefore selected it for further observation, testing, and asexual reproduction; such reproduction of the variety having been accomplished in my experimental orchard—located as aforesaid—by top-working on mature orchard trees. These reproductions, when they came into bearing, confirmed all of the characteristics of the parent, and the most important of which are as follows:

The ripening period of the fruit of the instant variety is shortly after the Early Sun Grand nectarine (United States Plant Patent No. 1,420), but before the Sun Grand nectarine, and thus serves an intermediate market.

More specifically, the fruit of the present variety of nectarine ripens approximately ten days later than the Early Sun Grand nectarine, and—in further comparison thereto—is slightly larger in size and firmer of flesh, but with somewhat less red exterior color; is of better eating quality; and has leaves with globose instead of reniform glands.

In comparison to the Sun Grand nectarine the fruit of the present variety ripens approximately one week earlier; is slightly larger in size but shorter axially; has somewhat less red exterior color; is not quite as firm of flesh, but of better eating quality; and has sweet instead of bitter kernels.

The present variety may also be compared with the Star Grand nectarine (United States Plant Patent No. 1,327) by approximately the same ripening period and general similarity in fruit characteristics, but distinct in that here the winter chilling requirement is much lower. This variety bore very heavy crops following warm winters, whereas the Star Grand nectarine lost many buds and bore comparatively light crops. The present variety also differs in that the leaves have globose instead of reniform glands; flowers with large instead of small petals; and kernels which are sweet instead of bitter, the sweetness resembling that of an almond.

In the drawings:

Fig. 1 is an elevation showing two of the fruit, together with twigs and leaves.

Fig. 2 is a sectional elevation of one of the fruit with the stone exposed.

Referring now more specifically to the pomological details of this new and distinct variety of nectarine tree, the following is an outline description thereof; all major color plate identifications being by reference to Maerz and Paul Dictionary of Color:

Tree:
- *Size.*—Large.
- *Vigor.*—Vigorous.
- *Growth.*—Spreading.
- *Density.*—Open.
- *Shape.*—Vase formed.
- *Production.*—Productive.
- *Bearing.*—Regular bearer.

Trunk:
- *Size.*—Medium.
- *Texture.*—Medium.

Branches:
- *Size.*—Medium.
- *Color.*—Brown.
- *Lenticels.*—Medium number; medium size.

Leaves:
- *Size.*—Large to medium. Average length, 6⅜". Average width, 1½".
- *Margin.*—Crenate.
- *Petiole.*—Medium length; medium thickness.
- *Glands.*—Average number—four; globose. Position—usually two on petiole and one or two on blade.
- *Color.*—Top side—medium green (22–L–8). Under side—lighter green (22–K–6).

Flower Buds:
- *Size.*—Medium.
- *Length.*—Medium.

Flowers:
- *Dates of first and full bloom.*—About with the Sun Grand nectarine. Early to medium blooming period compared with other varieties.
- *Size.*—Large.
- *Petals.*—Large.

Fruit:
- *Maturity when described.*—Eating ripe.
- *Date of first picking.*—July 3, 1956.
- *Date of last picking.*—July 12, 1956.
- *Size.*—Uniform; large. Average diameter axially, 2⅝". Average transversely in suture plane, 2½".
- *Form.*—Uniform; symmetrical; globose to oblong.
- *Suture.*—Shallow.
- *Ventral surface.*—Rounded strongly. Lips—equal.
- *Cavity.*—Rounded. Average depth, ½". Average breadth, ⅝". Markings—red.
- *Base.*—Rounded.
- *Apex.*—Short; rounded.

Skin:
- *Thickness.*—Thick to medium.
- *Texture.*—Medium.
- *Down.*—Wanting.
- *Color.*—Yellow ground color (9–L–5), largely overspread with bright red (2–L–11 to 6–L–6 to 55–L–12); the lightest of which red shades from orange (9–L–8 to 9–L–11).

Flesh:
- *Juice.*—Moderate; rich.
- *Texture.*—Firm; meaty.
- *Fibers.*—Few.
- *Ripens.*—Even.
- *Flavor.*—Sub-acid.

*Aroma.*—Distinct.
*Eating Quality.*—Good.
*Color.*—Yellow (9–K–4, shading to 9–L–6), with red (2–K–7) near stone.

Stone:
*Type.*—Free; parts from flesh smoothly.
*Size.*—Medium. Average length, 1¾". Average breadth, 1 3/16". Average thickness, ⅞".
*Form.*—Ovoid.
*Hilum.*—Oblong.
*Apex.*—Rounded.
*Sides.*—Equal.
*Surface.*—Regularly furrowed near base; pitted from base to above center.
*Ridges.*—Rounded.
*Pits.*—Elongated.
*Ventral edge.*—Thick.
*Dorsal edge.*—Full, with shallow groove.
*Tendency to split.*—Slight.
*Color.*—Brown (15–A–12).

Use: Market; local; long distance shipping.
Keeping quality: Good.
Shipping quality: Good.

The tree and its fruit herein described may vary in slight detail due to climatic and soil conditions under which the variety may be grown.

The following is claimed:

A new and distinct variety of nectarine tree, as illustrated and described, which has a relatively low winter chilling requirement, and bears large, firm, yellow-fleshed, freestone fruit having smooth surfaced yellow skin largely overspread with a bright red shading from orange; characterized by a ripening period about ten days later than the Early Sun Grand nectarine, about one week earlier than the Sun Grand nectarine, and approximately with the Star Grand nectarine; further characterized—in comparison with said Early Sun Grand nectarine—by fruit which is larger in size and firmer of flesh, but with less red exterior color, of better eating quality, and leaves with globose instead of reniform glands; further characterized—in comparison with said Sun Grand nectarine—by fruit which is larger in size but shorter axially, with less red exterior color, not as firm of flesh but of better eating quality, and having sweet instead of bitter kernels; and further characterized—in comparison with said Star Grand nectarine—by the aforesaid lower winter chilling requirement, leaves with globose instead of reniform glands, flowers with large instead of small petals, and kernels which are sweet instead of bitter.

No references cited.